United States Patent [19]

Deminski

[11] Patent Number: 5,788,706

[45] Date of Patent: Aug. 4, 1998

[54] CONTACT LENS INSERTER/REMOVER

[76] Inventor: Kerry J. Deminski, 369 E. Green St., Nanticoke, Pa. 18634

[21] Appl. No.: 888,637

[22] Filed: Jul. 7, 1997

Related U.S. Application Data

[60] Provisional application No. 60/025,170, Aug. 29, 1996.
[51] Int. Cl.$^6$ ............................................. A61F 9/00
[52] U.S. Cl. ............................................. 606/107
[58] Field of Search .................................. 606/107, 166, 606/207, 208, 167

[56]  References Cited

U.S. PATENT DOCUMENTS

| | | | |
|---|---|---|---|
| 5,147,369 | 9/1992 | Wagner | 606/107 |
| 5,178,622 | 1/1993 | Lehner, II | 606/107 |
| 5,662,659 | 9/1997 | McDonald | 606/107 |

*Primary Examiner*—Michael Buiz
*Assistant Examiner*—Kevin Truong
*Attorney, Agent, or Firm*—Richard L. Huff

[57]  ABSTRACT

A device for inserting and removing contact lenses comprises a vertical riser which separates a horizontal supporting bar and a horizontal stabilizing base. On end of the supporting bar is attached to the riser and the other end holds a transparent holder for a contact lens. The stabilizing base extends away from the riser in the same direction as the supporting bar and provides stability to the apparatus. The contact lens holder has an alignment spot in its center. The stabilizing base has an alignment spot directly beneath the alignment spot of the contact lens holder. To insert a contact lens, the lens is placed on a moistened lens holder. The user aligns the two spots and approaches the lens while maintaining alignment. Once contact is made, the lens will adhere to the eye. Removal of the lens is carried out in a similar manner using a dry lens holder.

3 Claims, 1 Drawing Sheet

CONTACT LENS INSERTER/REMOVER

CROSS-REFERENCE TO RELATED APPLICATIONS

This application claims the benefit of the inventor's provisional application Ser. No. 60/025,170, filed Aug. 8, 1996 now pending.

BACKGROUND OF THE INVENTION

1. Field of the Invention

This invention is directed to a device for inserting and removing contact lenses and to methods for using this device.

2. Description of the Related Art

There is a plethora of devices on the market and in the literature for the insertion and removal of contact lenses. The device which the present inventor considers to be most closely related to the device of the present invention is found in U.S. Pat. No. 3,697,109 to Parrent. This patented device is complex in nature, relying on springs and electronic circuitry for proper use. Also, its excessive size makes its use while traveling an inconvenience. Other contact lens inserters and removers require the use of the wearer's hands to position the lenses properly. This becomes a problem if the wearer suffers from Parkinson's disease or other source of tremor. Also, simple clumsiness on the part of the wearer causes improper insertion or even loss of the contact lenses

SUMMARY OF THE INVENTION

The present invention is designed to provide an extremely simple and inexpensive device for the insertion and removal of contact lenses. It is of one piece in design with no moving parts. Correct insertion and removal of the contact lenses is virtually guaranteed each time. No hand movements are required for the insertion and removal procedures, so wearers without perfect small muscle control in the hands have no trouble inserting and removing contact lenses. The device of the present invention comprises a riser which separates an upper supporting bar from a lower stabilizing base. The upper supporting bar contains a transparent holder for a contact lens. There is an alignment spot in the center of the transparent holder. The lower stabilizing base contains an alignment spot directly below the stabilizing spot in the contact lens holder. Thus, by simply bending over the device and maintaining the two spots in alignment, the insertion or the removal of a contact lens is made possible in a very simple manner. When the contact lens is to be inserted into the eye, the contact lens holder is moistened to assure proper release of the contact lens to the eye. When the contact lens is to be removed from the eye, the contact lens holder is dried to ensure adherence of the contact lens to the contact lens holder. Thus, the present invention provides something which the prior art has not provided, a device which allows a simple, effective method of inserting and removing contact lenses which does not require small muscle control in the hands on the part of the wearer.

DESCRIPTION OF THE PREFERRED EMBODIMENTS

Figure 1:
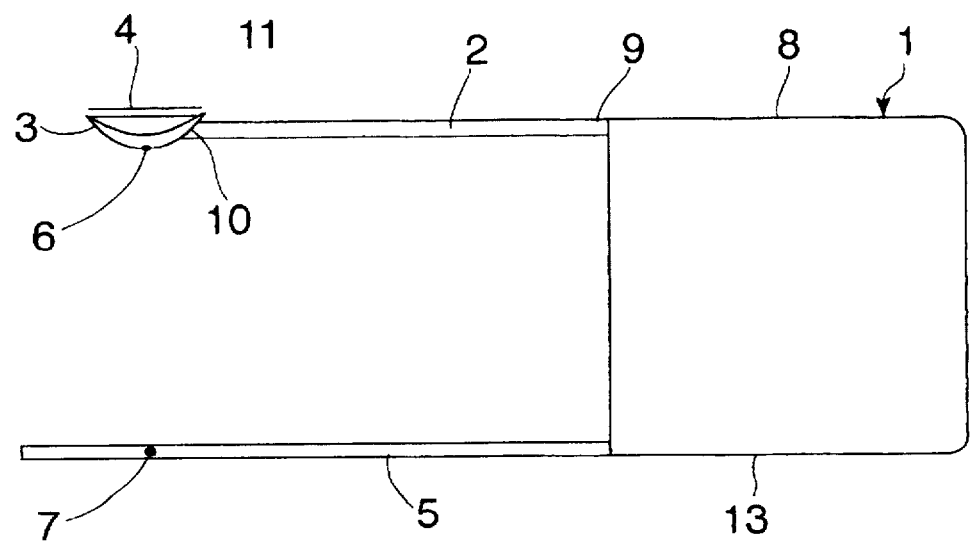
FIG. 1 is a side elevational view of the device of the present invention.
Figure 2:
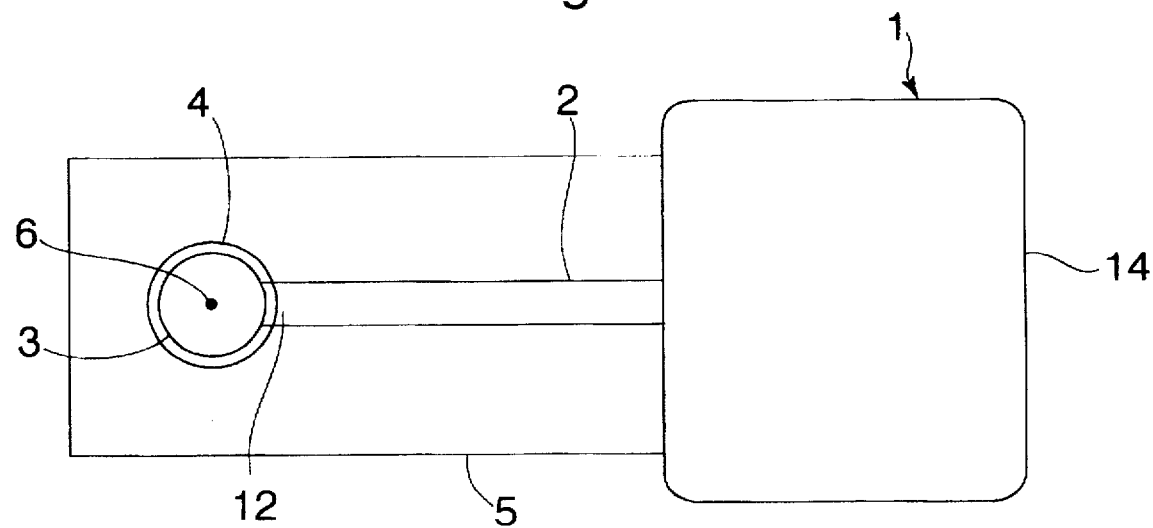
FIG. 2 is a top plan view of the device of this invention.

The invention will now be described in greater detail with reference to FIGS. 1 and 2. Like numbers refer to like parts throughout the description.

This invention provides for a riser 1 which extends from a stabilizing base 5 to a supporting bar 2. The purpose of the riser 1 is to maintain a constant distance between the stabilizing base 5 and the supporting bar 2. The riser 1 may be of any attractive shape, such as cylindrical, frusto-pyrmidal or frusto-conical although hexahedral is preferred. The riser 1 has a top surface 8, a bottom surface 13, and at least one side 14.

A supporting bar 2 extends horizontally from the riser 1 at the level of the top 8 of the riser 1. The supporting bar 2 has a proximal end 9 attached to the riser 1 and a distal end 12 attached to a lens holder 3.

The lens holder 3 is transparent, circular in shape when viewed from above, has a concave upper surface 11 and a convex lower surface 10. The lens holder 3 has a centrally located alignment spot 6. The size of the lens holder 3 is such that it is slightly smaller in diameter than a contact lens 4 in order to make all edges of the contact lens 4 capable of contacting the eye without allowing the lens holder 3 to contact the eye.

A stabilizing base 5 extends horizontally from the riser 1 at the of level of the bottom surface 13 of the riser 1. The stabilizing base 5 is flat and wide in order to provide maximum stability to the supporting bar 2. The stabilizing base 5 contains an alignment spot 7 at a point which is directly below the alignment spot 6 of the lens holder 3.

The device may be made of any material as long as the lens holder 3 is transparent. Preferably, the entire device is made of the same material, and preferably that material is transparent plastic.

For use in inserting a contact lens 4 into the eye, the lens holder 3 is moistened with a physiologically safe liquid such as eye drops or contact lens solution then the contact lens 4 is placed onto the upper concave surface 11 of the contact lens holder 3. The wearer bends over the device of this invention so that the alignment spot 6 of the lens holder 3 is aligned with the alignment spot 7 of the stabilizing base 5. The wearer maintains alignment with these two spots while approaching the supported contact lens 4. When contact is made between the eye and the contact lens 4, the liquid in the lens holder 3 allows easy transfer of the contact lens 4 from the lens holder 3 to the eye.

The device may be turned 180° for use with the other eye if two contact lenses are worn. This turning is necessary in order to prevent contact of the bridge of the nose with the supporting bar 2. It is, of course, possible to prepare a support bar 2 which is concave downwardly so as to avoid the step of turning the device.

To use the device in removing contact lenses, the upper concave surface 11 of the lens holder 3 is dried. This presents a surface to which the contact lens 4 will adhere. The wearer aligns the two alignment spots and maintains this alignment as the wearer's eye approaches the upper concave surface 11 of the contact lens holder 3. When the contact lens touches the dry lens holder 3 it adheres to the lens holder 3 and the wearer can pull away from the device, leaving the contact lens 4 resting on the lens holder 3.

While a specific embodiment of an apparatus for inserting and removing contact lenses has been disclosed in the foregoing description, it will be understood that various modifications within the spirit of the invention may occur to those skilled in the art. Therefore, it is intended that no limitations be placed on the invention except as defined by the scope of the appended claims.

I claim:

1. A device for inserting and removing contact lenses, comprising:

(a) a riser having a top surface, a bottom surface, and at least one side, (b) a supporting bar extending horizontally from the top surface of the riser, (c) a transparent lens holder having lower convex and upper concave circular surfaces attached to the supporting bar, said lens holder having an alignment spot in its center, and (d) a stabilizing base extending horizontally from the bottom surface of the riser, which stabilizing base contains an alignment spot at a point which is directly below the alignment spot of the lens holder.

2. A method of inserting a contact lens using the device of claim 1, which comprises:

(a) moistening the lens holder with eye drops or contact lens fluid, (b) placing the contact lens in the upper concave surface of the lens holder, (c) bending over the device of claim 1 so that the alignment spot of the lens holder is aligned with the alignment spot of the stabilizing base, and (d) maintaining alignment of the alignment spots while approaching the supported contact lens until the contact lens is inserted.

3. A method of removing a contact lens using the device of claim 1, which comprises:

(a) drying the upper concave surface of the lens holder, (b) bending over the device of claim 1 so that the alignment spot of the lens holder is aligned with the alignment spot of the stabilizing base, (c) maintaining alignment of the alignment spots while approaching the upper concave surface of the lens holder, (d) contacting the contact lens with the upper concave surface of the lens holder so that the contact lens is adhered to the dry surface of the lens holder, and (e) moving away from the device, leaving the contact lens attached thereto.

* * * * *